(12) United States Patent
Shah et al.

(10) Patent No.: US 10,813,870 B2
(45) Date of Patent: Oct. 27, 2020

(54) MINERAL SUNSCREEN COMPOSITIONS WITH IMPROVED EFFICACY

(71) Applicant: L'OREAL, Paris (FR)

(72) Inventors: Anil Shah, East Windsor, NJ (US); Brian Scott Bodnar, Manasquan, NJ (US)

(73) Assignee: L'OREAL, Paris (FR)

( * ) Notice: Subject to any disclaimer, the term of this patent is extended or adjusted under 35 U.S.C. 154(b) by 6 days.

(21) Appl. No.: 16/146,215

(22) Filed: Sep. 28, 2018

(65) Prior Publication Data

US 2020/0101002 A1   Apr. 2, 2020

(51) Int. Cl.
| | | |
|---|---|---|
| *A61K 8/60* | (2006.01) |
| *A61K 8/06* | (2006.01) |
| *A61K 8/37* | (2006.01) |
| *A61K 8/40* | (2006.01) |
| *A61Q 17/04* | (2006.01) |
| *A61K 8/19* | (2006.01) |
| *A61K 8/27* | (2006.01) |
| *A61K 8/28* | (2006.01) |
| *A61K 8/29* | (2006.01) |
| *A61K 8/34* | (2006.01) |

(52) U.S. Cl.
CPC ............... *A61K 8/602* (2013.01); *A61K 8/06* (2013.01); *A61K 8/37* (2013.01); *A61K 8/40* (2013.01); *A61Q 17/04* (2013.01); *A61K 2800/30* (2013.01)

(58) Field of Classification Search
CPC . A61K 8/602; A61K 8/37; A61K 8/06; A61K 2800/30; A61K 8/40; A61K 8/19; A61K 8/27; A61K 8/28; A61K 8/29; A61K 8/347; A61Q 17/04
See application file for complete search history.

(56) References Cited

U.S. PATENT DOCUMENTS

| | | |
|---|---|---|
| 8,496,917 B2 | 7/2013 | Chaudhuri et al. |
| 10,004,671 B2 | 6/2018 | Bevacqua et al. |
| 2006/0083698 A1 | 4/2006 | Candau |

(Continued)

FOREIGN PATENT DOCUMENTS

| | | | | |
|---|---|---|---|---|
| EP | 2087894 | * | 8/2009 | ......... A61K 31/7034 |
| WO | WO-2012/174096 A2 | | 12/2012 | |

(Continued)

OTHER PUBLICATIONS

"Eye Duty Triple Remedy," MINTEL Database, 2018, pp. 1-74 http://www.gnpd.com.

(Continued)

*Primary Examiner* — Trevor Love
(74) *Attorney, Agent, or Firm* — Polsinelli PC (57) ABSTRACT

Mineral sunscreen compositions having improved efficacy are described. The mineral sunscreen compositions include: (a) one or more mineral UV filtering agents; (b) one or more stilbenoids; (c) ethylhexylmethoxycrylene. (d) diethylhexyl syringylidenemalonate; and (e) a cosmetically acceptable carrier. The mineral sunscreen compositions provide a high sun protection factor (SPF) without requiring high amounts of mineral UV filtering agents. Also, the mineral sunscreen compositions are less opaque and white than traditional mineral sunscreen compositions making them aesthetically appealing to consumers.

17 Claims, 2 Drawing Sheets

(56) References Cited

U.S. PATENT DOCUMENTS

| | | |
|---|---|---|
| 2006/0083699 A1 | 4/2006 | Candau |
| 2006/0104924 A1 | 5/2006 | Candau |
| 2006/0263321 A1* | 11/2006 | Bissett ............... A61K 8/37 424/70.13 |
| 2010/0254923 A1 | 10/2010 | Galdi et al. |
| 2012/0015016 A1 | 1/2012 | Galdi et al. |
| 2013/0230474 A1 | 9/2013 | Tanner |
| 2013/0243834 A1 | 9/2013 | Tanner |
| 2013/0266621 A1* | 10/2013 | Lerg ............... A61K 8/27 424/401 |
| 2015/0023895 A1 | 1/2015 | Finley et al. |

FOREIGN PATENT DOCUMENTS

| | | |
|---|---|---|
| WO | WO-2014/114888 A2 | 7/2014 |
| WO | WO-2017/189301 A1 | 11/2017 |

OTHER PUBLICATIONS

International Search Report and Written Opinion dated Dec. 20, 2019 for corresponding PCT Application No. PCT/US2019/053349.

* cited by examiner

MINERAL SUNSCREEN COMPOSITIONS WITH IMPROVED EFFICACY

FIELD OF THE DISCLOSURE

The present disclosure relates to mineral sunscreen compositions, and to methods for using the mineral sunscreen compositions to protect keratinous substrates such as skin and hair from UV radiation.

BACKGROUND

The negative effects of exposure to ultraviolet ("UV") light are well known. Prolonged exposure to sunlight causes damage such as sunburn to the skin and dries out hair making it brittle. When skin is exposed to UV light having a wavelength of from about 290 nm to about 400 nm, long term damage can lead to serious conditions such as skin cancer.

UV light also contributes to aging by causing free radicals to form in the skin. Free radicals include, for example, singlet oxygen, hydroxyl radical, the superoxide anion, nitric oxide and hydrogen radicals. Free radicals attack DNA, membrane lipids and proteins, generating carbon radicals. These in turn react with oxygen to produce a peroxyl radical that can attack adjacent fatty acids to generate new carbon radicals. This cascade leads to a chain reaction producing lipid peroxidation products. Damage to the cell membrane results in loss of cell permeability, increased intercellular ionic concentration, and decreased ability to excrete or detoxify waste products. The end result is a loss of skin elasticity and the appearance of wrinkles. This process is commonly referred to as photo-aging.

Sunscreens can be used to protect against UV damage and delay the signs of aging. The degree of UV protection afforded by a sunscreen composition is directly related to the amount and type of UV filters contained therein. The higher the amount of UV filters, the greater the degree of UV protection. Nevertheless, it is desirable to achieve the best photo protection efficacy with the lowest amount of UV filters. In particular, it is especially desirable to achieve high photoprotection with the lowest amount of UV filters when formulating with mineral UV filtering agents, since mineral UV filtering agents also result in a white color when applied to the skin when higher amounts are used in cosmetic formulations. The inventors of the instant disclosure discovered ways to attain Sun Protection Factor values that were not previously attainable with such low amounts of overall UV filters.

SUMMARY OF THE INVENTION

The instant disclosure relates to sunscreen compositions that provide a surprisingly high degree of efficacy and are aesthetically pleasing. The sunscreen compositions include mineral UV filtering agents, which are known to be non-irritating, natural, and gentle to the skin. One drawback with mineral-based sunscreen compositions is that they often appear white when applied to the skin. Consumers prefer sunscreen compositions to appear natural (unnoticeable). Developing mineral-based sunscreen products having a high Sun Protection Factor (SPF) that exhibit minimal or no whitening, however, is challenging.

The inventors of the instant case discovered a synergistic combination of ingredients that improve SPF without causing unacceptable whitening when applied to the skin. This synergism allows for the attainment of a high SPF without requiring high amounts of mineral-based UV filtering agents. The desired SPF can be attained using less mineral UV filtering agents, thereby reducing the whiteness of the composition. The sunscreen compositions typically include:
(a) one or more mineral UV filtering agents;
(b) one or more stilbenoids;
(c) ethylhexylmethoxycrylene;
(d) diethylhexyl syringylidenemalonate; and
(e) a cosmetically acceptable carrier.

Ethylhexylmethoxycrylene and diethylhexyl syringylidenemalonate have been used to boost the SPF of organic UV filtering agents. These compounds boost the SPF of organic UV filtering agent because they act as highly efficient singlet state quenchers. Organic UV filtering agents absorb UV light, thereby generating an excited singlet or triplet state in the molecule, resulting in the molecule being susceptible to decomposition and loss of photoprotection efficacy. Mineral UV filtering agents do not require quenching by photostabillizing compounds because they remain photostable. Therefore, prior to the inventors' discovery, there was no reason to specifically include these compounds with mineral UV filtering agents. It was not known that ethylhexylmethoxycrylene, diethylhexyl syringylidenemalonate, or mixtures thereof, could provide any particular benefit or enhancement to mineral UV filtering agents.

The inventors discovered that the inclusion of a combination of stilbenoids, ethylhexyl-methoxycrylene, and diethylhexyl syringylidenemalonate surprisingly boosts (improves) the SPF of mineral UV filtering agents, which allows for reduced amounts of mineral UV filtering agents in the sunscreen compositions. Reducing the amounts of mineral UV filtering agents reduces the whitening and improves overall aesthetics of the sunscreen formulation, compared to an equivalent composition at the same SPF without the combination.

In particular, the use of particular combinations of stilbenoids, ethylhexyl methoxycrylene, and diethylhexyl syringylidenemalonate, results in an improved (boosted) SPF beyond that which is attainable by using an equivalent amount of only ethylhexyl methoxycrylene or only diethylhexyl syringylidenemalonate. While not wishing to be bound by any particular theory, it is believed that the combinations boost the SPF of the mineral UV filtering agents and reduce whiteness by allowing for use of less mineral UV filtering agents, which cause whitening of sunscreen formulations after application to skin.

In addition to the mineral sunscreen compositions described herein, the present disclosure relates to methods for protecting a keratinous substrate from ultraviolet (UV) radiation and to methods of absorbing ultraviolet light using the mineral sunscreen compositions. Such methods comprise application of a sunscreen composition to a keratinous substrate such as the skin and/or hair, and subjecting the keratinous substrate to ultraviolet radiation. Additionally, methods for boosting the SPF of mineral UV filtering agents and methods for reducing whiteness of mineral sunscreen compositions are described.

BRIEF DESCRIPTION OF THE DRAWINGS

Implementations of the present technology will now be described, by way of example only, with reference to the attached figures, wherein.

It should be understood that the various aspects are not limited to the arrangements and instrumentality shown in the figures.

DETAILED DESCRIPTION

Where the following terms are used in this specification, they are used as defined below.

The terms "comprising," "having," and "including" are used in their open, non-limiting sense.

The terms "a" and "the" are understood to encompass the plural as well as the singular.

The term "mineral UV filtering agent" is interchangeable with the terms "mineral UV screening agent," "inorganic UV filtering agent," "inorganic UV screening agent," "mineral UV filter, and "inorganic UV filter." Mineral UV filtering agents are compounds that do not include any carbon atoms in their chemical structures that are capable of screening out or absorbing UV radiation between 280 and 400 nm.

The compositions and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "treat" (and its grammatical variations) as used herein refers to the application of compositions of the present disclosure onto the surface of skin and/or hair. The term 'treat" (and its grammatical variations) as used herein also refers to contacting the skin or hair with the compositions of the present disclosure.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

"Cosmetically acceptable" means that the item in question is compatible with a keratinous substrate such as skin and hair. For example, a "cosmetically acceptable carrier" means a carrier that is compatible with a keratinous substrate such as skin and hair.

The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counter-ion. This list of counter-ions, however, is non-limiting.

The phrase "stable emulsion" refers to a composition that does not undergo phase separation up to a temperature of 45 C.° for at least two weeks.

The expression "inclusive" for a range of concentrations means that the limits of the range are included in the defined interval.

"Volatile", as used herein, means having a flash point of less than about 100° C.

"Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

The term "weight ratio" or "mass ratio" as used herein, references the amount of a substance in proportion to a mixture containing said substance, and is calculated by dividing the amount of said substance by weight contained in the mixture by the weight of the mixture containing said substance. As an example, a weight ratio of 0.4 for substance A in a mixture of A, B, and C indicates that the weight of substance A divided by the total weight of substances A, B, and C is 0.4.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The instant disclosure relates to sunscreen compositions that provide a surprisingly high degree of efficacy and are aesthetically pleasing. The sunscreen compositions include mineral UV filtering agents, which are known to be non-irritating, natural, and gentle to the skin. The inventors discovered that a synergistic combination of stilbenoids, ethylhexylmethoxycrylene, and diethylhexyl syringylidenemalonate unexpectedly boost the SPF of mineral-based sunscreen compositions. This synergism allows for the attainment of a high SPF without requiring high amounts of mineral-based UV filtering agents, thereby reducing the whiteness associated with mineral-based sunscreen compositions. The sunscreen compositions typically include:
(a) one or more mineral UV filtering agents;
(b) one or more stilbenoids;
(c) ethylhexylmethoxycrylene;
(d) diethylhexyl syringylidenemalonate; and
(e) a cosmetically acceptable carrier.

Non-limiting examples of useful mineral filtering agents include titanium dioxide, zinc oxide, iron oxides, cerium oxides, zirconium oxides, and a mixture thereof. Non-limiting examples of useful stilbenoids include piceid, resveratrol, piceatannol, pterostilbene, and a mixture thereof. The sunscreen compositions may optionally include organic UV filtering agents but organic UV filtering agents are certainly not needed and may optionally be excluded. Therefore, the sunscreen compositions may be free or essentially free of organic UV filtering agents. In some instances, the sunscreen compositions may be free or essentially free of butyl methoxydibenzoylmethane (avobenzone) and ethylhexyl methoxycinnamate (octinoxate).

The weight ratio of piceid, ethylhexylmethoxycrylene, and diethylhexyl syringylidenemalonate relative to the total weight of the combination of piceid, ethylhexylmethoxycrylene, and diethylhexyl syringylidenemalonate may be as follows:
about 0.1 to about 0.5 of the one or more stilbenoids;
about 0.3 to about 0.7 of ethylhexylmethoxycrylene; and
about 0.1 to 0.5 of diethylhexyl syringylidenemalonate.

The stilbenoid(s), ethylhexylmethoxycrylene, and diethylhexyl syringylidenemalonate are typically in amounts sufficient to boost the in vitro SPF of the sunscreen composition by at least 5% in comparison to an otherwise identical sunscreen composition in which the total amount of the stilbenoid(s), ethylhexylmethoxycrylene, and diethylhexyl syringylidenemalonate is replaced with only ethylhexylmethoxycrylene. Furthermore, the stilbenoid(s), ethylhexylmethoxycrylene, and diethylhexyl syringylidenemalonate are typically in amounts sufficient to boost the in vitro SPF of the sunscreen composition by at least 5% in comparison to an otherwise identical sunscreen composition in which the total amount of stilbenoid(s), ethylhexylmethoxycrylene, and diethylhexyl syringylidenemalonate is replaced with only diethylhexyl syringylidenemalonate.

Mineral UV Filtering Agents

Non-limiting examples of mineral UV filtering agent include treated or untreated metal oxides such as, for example, pigments or nanopigments of titanium oxide (amorphous or crystallized in rutile and/or anatase form), of iron oxide, of zinc oxide, of zirconium oxide or of cerium oxide. Particularly preferred mineral UV filtering agents include titanium dioxide and/or zinc oxide.

In some instances, the mean particle size may be about 5 nm to about 25 µm, about 10 nm to about 10 µm, or about 15 nm to about 5 µm. The mineral UV filtering agents may be nano-pigments having a mean particle size of about 5 nm to about 100 nm, about 5 nm to about 75 nm, or about 10 nm to 50 nm. Larger particles sizes may also be useful, for example about 1 µm to about 25 µm, about 5 µm to about 20 µm, or about 10 µm to about 15 µm.

Treated pigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal (titanium or aluminium) alkoxides, polyethylene, silicones, proteins (collagen or elastin), alkanolamines, silicon oxides, metal oxides, sodium hexametaphosphate, alumina or glycerol.

The treated pigments may be titanium oxides treated with:
silica and alumina, such as the products "Microtitanium Dioxide MT 500 SA" and "Microtitanium Dioxide MT 100 SA" from the company Tayca, and the products "Tioveil Fin", "Tioveil OP", "Tioveil MOTG" and "Tioveil IPM" from the company Tioxide;
alumina and aluminium stearate, such as the product "Microtitanium Dioxide MT 100 T" from the company Tayca;
alumina and aluminium laurate, such as the product "Microtitanium Dioxide MT 100 S" from the company Tayca;
iron oxides and iron stearate, such as the product "Microtitanium Dioxide MT 100 F" from the company Tayca;
silica, alumina and silicone, such as the products "Microtitanium Dioxide MT 100 SAS", "Microtitanium Dioxide MT 600 SAS" and "Microtitanium Dioxide MT 500 SAS" from the company Tayca;
sodium hexametaphosphate, such as the product "Microtitanium Dioxide MT 150 W" from the company Tayca;
octyltrimethoxysilane, such as the product "T-805" from the company Degussa;
alumina and stearic acid, such as the product "UVT-M160" from the company Kemira;
alumina and glycerol, such as the product "UVT-M212" from the company Kemira;
alumina and silicone, such as the product "UVT-M262" from the company Kemira.

Other titanium oxide pigments treated with a silicone are $TiO_2$ treated with octyltrimethylsilane and for which the mean size of the elementary particles is between 25 and 40 nm, such as the product sold under the trade name "T805" by the company Degussa Silices, $TiO_2$ treated with a polydimethylsiloxane and for which the mean size of the elementary particles is 21 nm, such as the product sold under the trade name "70250 Cardre UF TiO2SI3" by the company Cardre, anatase/rutile TiO$_2$ treated with a polydimethylhydrogenosiloxane and for which the mean size of the elementary particles is 25 nm, such as the product sold under the trade name "Microtitanium Dioxide USP Grade Hydrophobic" by the company Color Techniques.

Uncoated titanium oxide pigments are sold, for example, by the company Tayca under the trade names "Microtitanium Dioxide MT 500 B" or "Microtitanium Dioxide MT 600 B", by the company Degussa under the name "P 25", by the company Wackher under the name "Oxyde de titane transparent PW", by the company Myoshi Kasei under the name "UFTR", by the company Tomen under the name "ITS" and by the company Tioxide under the name "Tioveil AQ".

The uncoated zinc oxide pigments are, for example:
those sold under the name "Z-Cote" by the company Sunsmart;
those sold under the name "Nanox" by the company Elementis; and
those sold under the name "Nanogard WCD 2025" by the company Nanophase Technologies.

The coated zinc oxide pigments are, for example:
those sold under the name "Zinc Oxide CS-5" by the company Toshibi (ZnO coated with polymethylhydrogenosiloxane);
those sold under the name "Nanogard Zinc Oxide FN" by the company Nanophase Technologies (as a 40% dispersion in Finsolv TN, $C_{12}$-$C_{15}$ alkyl benzoate);
those sold under the name "Daitopersion ZN-30" and "Daitopersion ZN-50" by the company Daito (dispersions in cyclopolymethylsiloxane/oxyethylenated polydimethylsiloxane, containing 30% or 50% of nanozinc oxides coated with silica and polymethylhydrogenosiloxane);
those sold under the name "NFD Ultrafine ZNO" by the company Daikin (ZnO coated with perfluoroalkyl phosphate and copolymer based on perfluoroalkylethyl as a dispersion in cyclopentasiloxane);
those sold under the name "SPD-Z1" by the company Shin-Etsu (ZnO coated with silicone-grafted acrylic polymer, dispersed in cyclodimethylsiloxane);
those sold under the name "Escalol Z100" by the company ISP (alumina-treated ZnO dispersed in an ethylhexyl methoxycinnamate/PVP-hexadecene/methicone copolymer mixture);
those sold under the name "Fuji ZNO-SMS-10" by the company Fuji Pigment (ZnO coated with silica and polymethylsilsesquioxane); and
those sold under the name "Nanox Gel TN" by the company Elementis (ZnO dispersed at a concentration of 55% in $C_{12}$-$C_{15}$ alkyl benzoate with hydroxystearic acid polycondensate).

The uncoated cerium oxide pigments are sold under the name "Colloidal Cerium Oxide" by the company Rhone-Poulenc. The uncoated iron oxide nanopigments are sold, for example, by the company Arnaud under the names "Nanogard WCD 2002 (FE 45B)", "Nanogard Iron FE 45 BL AQ", "Nanogard FE 45R AQ" and "Nanogard WCD 2006 (FE 45R)" or by the company Mitsubishi under the name "TY-220". The coated iron oxide nanopigments are sold, for example, by the company Arnaud under the names "Nanogard WCD 2008 (FE 45B FN)", "Nanogard WCD 2009 (FE 45B 556)", "Nanogard FE 45 BL 345" and "Nanogard FE 45 BL" or by the company BASF under the name "Transparent Iron Oxide".

Mixtures of metal oxides may also be used, especially of titanium dioxide and of cerium dioxide, including the silica-coated equal-weight mixture of titanium dioxide and of cerium dioxide, sold by the company Ikeda under the name "Sunveil A", and also the alumina, silica and silicone-coated mixture of titanium dioxide and of zinc dioxide, such as the product "M 261" sold by the company Kemira, or the alumina, silica and glycerol-coated mixture of titanium dioxide and of zinc dioxide, such as the product "M 211" sold by the company Kemira.

The total amount of mineral UV filtering agents in the mineral sunscreen compositions can vary but is typically about 1 to about 30 wt. %, based on the total weight of the sunscreen composition. In some instances, the total amount of mineral UV filtering agents may be about 1 to about 25 wt. %, about 1 to about 20 wt. %, about 1 to about 15 wt. %, about 1 to about 10 wt. %, about 5 to about 30 wt. %, about 5 to about 25 wt. %, about 5 to about 20 wt. %, about 5 to about 5 wt. %, about 5 to about 10 wt. %, based on the total weight of the sunscreen composition.

Stilbenoids

Stilbenoids are secondary products of heartwood formations in trees that possess phytoalexin properties. In chemical terms, they are derivatives of stilbene, often containing one or more phenolic functional groups. In biochemical terms, they belong to the family of phenylalanine derivatives known as phenylpropanoids. Much of their biosynthetic pathway is shared with those of the aromatic chalconoids, such as chalcone.

A well-characterized botanical stilbenoid is resveratrol (3,5,4'-trihydroxy-trans-stilbene), a resorcinol derivative first isolated in 1939 from the white hellebore (Veratrum album), which is found in the skin of red grapes, and in other fruits and nuts including berries and peanuts. Non-limiting examples of useful stilbenoids in the context of the instant disclosure include piceid, resveratrol, piceatannol, pterostilbene, and a mixture thereof. In some instances, piceid and resveratrol are preferred stilbenoids; piceid being the most preferred.

The total amount of the stilbenoids in the mineral sunscreen compositions can vary but is typically about 0.1 to 8 wt. %, based on the total weight of the sunscreen composition. In some instances, the total amount of stilbenoids in the sunscreen composition is about 0.1 to about 7 wt. %, about 0.1 to about 6 wt. %, about 0.1 to about 5 wt. %, 0.1 to about 4 wt. %, or about 0.1 to about 3 wt. %, preferably about 0.1 to about 5 wt. %, more preferably about 0.1 to about 3 wt. %, based on the total weight of the sunscreen compositions.

Notwithstanding the amounts of stilbenoids described above, the weight ratio of the total amount of stilbenoids in the sunscreen composition relative to the total amount of the combination of the stilbenoids, ethylhexylmethoxycrylene, and diethylhexyl syringylidenemalonate may be about 0.1 to about 0.5. In some cases, the weight ratio may be about 0.1 to about 0.4, or about 0.2 to about 0.4.

Ethylhexylmethoxycrylene

The total amount of ethylhexylmethoxycrylene in the mineral sunscreen composition can vary but is typically about 0.1 to about 8 wt. %, based on the total weight of the sunscreen composition. In some cases, the total amount of ethylhexylmethoxycrylene in the sunscreen composition may be about 0.1 to about 7 wt. %, about 0.1 to about 6 wt. %, about 0.1 to about 5 wt. %, 0.1 to about 4 wt. %, or about 0.1 to about 3 wt. %, preferably about 0.1 to about 5 wt. %, more preferably about 0.1 to about 3 wt. %, based on the total weight of the sunscreen compositions.

Notwithstanding the amounts of ethylhexylmethoxycrylene described above, the weight ratio of the total amount of ethylhexylmethoxycrylene in the sunscreen composition relative to the total amount of the combination of the stilbenoids, the ethylhexylmethoxycrylene, and the diethylhexyl syringylidenemalonate may be about 0.25 to about 0.75. In some cases, the weight ratio may be about 0.3 to about 0.7, about 0.3 to about 0.6, about 0.3 to about 0.65, or about 0.3 to about 0.6.

Diethylhexyl Syringylidenemalonate

The total amount of diethylhexyl syringylidenemalonate in the mineral sunscreen composition can vary but is typically about 0.1 to about 8 wt. %, based on the total weight of the sunscreen composition. In some cases, the total amount of diethylhexyl syringylidenemalonate in the sunscreen composition may be about 0.1 to about 7 wt. %, about 0.1 to about 6 wt. %, about 0.1 to about 5 wt. %, 0.1 to about 4 wt. %, or about 0.1 to about 3 wt. %, preferably about 0.1 to about 5 wt. %, more preferably about 0.1 to about 3 wt. %, based on the total weight of the sunscreen compositions.

Notwithstanding the amounts of diethylhexyl syringylidenemalonate described above, the weight ratio of the total amount of diethylhexyl syringylidenemalonate in the sunscreen composition relative to the total amount of the combination of the stilbenoids, ethylhexylmethoxycrylene, and diethylhexyl syringylidenemalonate may be about 0.1 to about 0.5. In some cases, the weight ratio may be about 0.1 to about 0.45, or about 0.15 to about 0.4.

Combination of Stilbenoids, Ethylhexylmethoxycrylene, and Diethylhexyl Syringylidenemalonate As already mentioned, stilbenoids, ethylhexylmethoxycrylene, and diethylhexyl syringylidenemalonate synergistically interact in combination to unexpectedly boost the SPF of mineral UV filtering agents. Thus, the amount of stilbenoids, ethylhexylmethoxycrylene, and diethylhexyl syringylidenemalonate and the weight ratio of these compounds with respect to each other in the sunscreen compositions are sufficient to improve the SPF of the sunscreen composition.

In one embodiment, the stilbenoid(s), ethylhexylmethoxycrylene, and diethylhexyl syringylidenemalonate are in amounts sufficient to boost the in vitro SPF of the sunscreen composition by at least 5% in comparison to an otherwise identical sunscreen composition in which the total amount of the stilbenoid(s), ethylhexylmethoxycrylene, and diethylhexyl syringylidenemalonate is replaced with only ethylhexylmethoxycrylene. In some cases, the in vitro SPF is boosted by at least 6%, at least 7%, at least 8%, at least 9%, or at least 10%.

In another embodiment, the stilbenoid(s), ethylhexylmethoxycrylene, and diethylhexyl syringylidenemalonate are in amounts sufficient to boost the in vitro SPF of the sunscreen composition by at least 5% in comparison to an otherwise identical sunscreen composition in which the total amount of the stilbenoid(s), the ethylhexylmethoxycrylene, and the diethylhexyl syringylidenemalonate is replaced with only diethylhexyl syringylidenemalonate. In some cases, the in vitro SPF is boosted by at at least 8%, or at least 10%, at least 12%, at least 15%, at least 18%, or at least 20%.

The weight ratio of the stilbenoids, ethylhexylmethoxycrylene, and diethylhexyl syringylidenemalonate relative to each other can be useful for attaining the desired boost in SPF. Accordingly, in some embodiments, the weight ratio of the stilbenoids, ethylhexylmethoxycrylene, and diethylhexyl syringylidenemalonate relative to the total weight of the combination of stilbenoids, ethylhexylmethoxycrylene, and diethylhexyl syringylidenemalonate is as follows:

about 0.1 to about 0.5, preferably about 0.1 to about 0.4, more preferably about 0.2 to about 0.4 of the one or more stilbenoids;

about 0.25 to about 0.75, preferably about 0.3 to about 0.7, more preferably about 0.3 to about 0.6 of ethylhexylmethoxycrylene; and about 0.1 to about 0.5, preferably, about 0.1 to about 0.45, more preferably about 0.15 to about 0.4 of diethylhexyl syringylidenemalonate.

The total amount of the combination of stilbenoids, ethylhexylmethoxycrylene, and diethylhexyl syringylidenemalonate in the sunscreen compositions can vary but is typically about 0.5 to about 10 wt. %, based on the total weight of the sunscreen composition. In some instances, the total amount of the combination of stilbenoids, ethylhexylmethoxycrylene, and diethylhexyl syringylidenemalonate in the sunscreen compositions may be about 0.5 to about 8 wt. %, about 0.5 to about 5 wt. %, about 0.5 to about 4 wt. %, about 0.5 to about 3 wt. %, about 1 to about 10 wt. %, about 1 to about 8 wt. %, about 1 to about 5 wt. %, about 1 to about 4 wt. %, or about 1 to about 3 wt. %, based on the total weight of the sunscreen composition. Regardless of the total amount of the stilbenoids, ethylhexylmethoxycrylene, and diethylhexyl syringylidenemalonate in the sunscreen compositions, the stilbenoids, ethylhexylmethoxycrylene, and diethylhexyl syringylidenemalonate may be present in the sunscreen composition according to the weight ratios set forth above.

Cosmetically Acceptable Carrier

The sunscreen compositions include a cosmetically acceptable carrier. The phrase "cosmetically acceptable" means that the material is compatible with skin and hair. For example, "cosmetically acceptable carrier" means a carrier that is compatible with skin and hair, and is acceptable for application to the body.

The cosmetically acceptable carrier may include, for example, water and/or water soluble solvents. Non-limiting examples of cosmetically acceptable carriers include glycerin, C1-4 alcohols, organic solvents, fatty alcohols, fatty ethers, fatty esters, polyols, glycols, vegetable oils, mineral oils, liposomes, laminar lipid materials, water, or any combinations thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

The total amount of cosmetically acceptable carrier can vary, but in some instances may be about 50 to about 95 wt. %, based on the total weight of the sunscreen composition.

In some instances, the total amount of cosmetically acceptable carrier is about 55 to about 95 wt. %, about 60 to about 95 wt. %, about 70 to about 95 wt. %, about 75 to about 95 wt. %, about 50 to about 90 wt. %, about 60 to about 90 wt. %, about 70 to about 90 wt. %, or about 75 to about 90 wt. %, based on the total weight of the sunscreen composition.

Oils/Emollients

Oils and/or emollients may optionally be included in the hair treatment compositions. Examples of oils/emollients that may be included in the sunscreen compositions include: hydrocarbon-based oils of plant origin, such as liquid triglycerides of fatty acids containing from 4 to 10 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, jojoba oil, shea butter oil and caprylyl glycol; synthetic esters and ethers, especially of fatty acids, for instance Purcellin oil, 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate, or isopropyl lauroyl sarcosinate, sold especially under the trade name Eldew SL 205 by the company Ajinomoto; linear or branched hydrocarbons, of mineral or synthetic origin, such as volatile or non-volatile liquid paraffins, and derivatives thereof, petroleum jelly, polydecenes, isohexadecane, isododecane, hydrogenated polyisobutene such as Parleam oil, or the mixture of n-undecane ($C_{11}$) and of n-tridecane ($C_{13}$) sold under the reference Cetiol UT by the company Cognis; fluoro oils that are partially hydrocarbon-based and/or silicone-based, for instance those described in document JP-A-2 295 912; silicone oils, for instance volatile or non-volatile polymethylsiloxanes (PDMS) with a linear or cyclic silicone chain, which are liquid or pasty at room temperature, in particular volatile silicone oils, especially cyclopolydimethylsiloxanes (cyclomethicones) such as cyclohexadimethylsiloxane and cyclopentadimethylsiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes; mixtures thereof.

Additional specific examples of oils/emollients include cocoglyceride, cyclomethicone, dimethicone, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of $C_9$-$C_{15}$ alcohols, isononyl iso-nonanoate, alkanes, mineral oil, silicone, dimethyl polysiloxane, ether, polyoxypropylene butyl ether, polyoxypropylene cetyl ether, $C_{12}$-$C_{15}$ alkyl benzoate, aryl alkyl benzoate, Isopropyl Lauroyl sarcosinate, and any combinations thereof.

The total amount of oils and/or emollients in the sunscreen composition, if present, may vary but may be about 1 to about 75 wt. %, based on the total weight of the sunscreen composition. In some instances, the total amount of oils and/or emollients may be about 1 to about 60 wt. %, about 1 to about 50 wt. %, about 1 to about 20 wt. %, about 5 to about 70 wt. %, about 5 to about 60 wt. %, about 5 to about 50 wt. %, about 10 to about 60 wt. %, about 10 to about 50 wt. %, about 25 to about 75 wt. %, or about 30 to about 60 wt. %, based on the total weight of the sunscreen composition.

Film Formers

Film-formers may be incorporated into the sunscreen compositions to ensure even coverage of UV filters and can be used to render the composition water resistant. The film former is typically a hydrophobic material that imparts film forming and/or waterproofing characteristics. One such agent is polyethylene, which is available from New Phase Technologies as Performalene® 400, a polyethylene having a molecular weight of 400. Another suitable film former is polyethylene 2000 (molecular weight of 2000), which is available from New Phase Technologies as Performalene®. Yet, another suitable film former is synthetic wax, also available from New Phase Technologies as Performa® V-825. Other typical film-formers include acrylates/acrylamide copolymer, acrylates copolymer, acrylates/$C_{12}$-$C_{22}$ alkylmethacrylate copolymer, polyethylene, waxes, VP/dimethiconylacrylate/polycarbamylpolyglycol ester, butylated PVP, PVP/hexadecene copolymer, octadecene/MA copolymer, PVP/eicosene copolymer, tricontanyl PVP, Brassica Campestris/Aleuritis Fordi Oil copolymer, decamethyl cyclopentasiloxane (and) trimethylsiloxysilicate, and mixtures thereof. In some cases, the film former is acrylates/$C_{12}$-$C_{22}$ alkylmethacrylate copolymer sold under the tradename Allianz OPT® by ISP.

Many of the common film-forming polymers included in sunscreen compositions are not soluble in ethanol (such as PVP/Eicosene copolymer). A common film-former employed in ethanol based sunscreen products is Dermacryl LT or Dermacryl 79 marketed by Akzo Nobel (INCI Name: acrylates/octylacrylamide copolymner). Dermacryl LT (CAS Number: 80570-62-3) is a hydrophobic, high molecular weight carboxylated acrylic copolymer. It functions as a film-former in a broad range of cosmetic formulations, imparting waterproofing, increased occlusivity and decreased rub-off of actives.

The total amount of film forming in the sunscreen compositions, if present, may vary but is typically about 0.1 to about 40 wt. %, based on the total weight of the sunscreen composition. In some instances, the total amount of film formers may be about 0.1 to about 30 wt. %, about 0.1 to about 20 wt. %, about 0.1 to about 10 wt. %, about 1 to about 40 wt. %, about 1 to about 30 wt. %, about 1 to about 20 wt. %, or about 1 to about 10 wt. %, based on the total weight of the sunscreen composition.

Emulsifiers

The sunscreen compositions may optionally include at least one emulsifier such as an amphoteric, anionic, cationic or nonionic emulsifier, used alone or as a mixture, and optionally a co-emulsifier. Emulsifiers are most often used when the sunscreen composition is in the form of an emulsion. The emulsifiers are chosen in an appropriate manner according to the emulsion to be obtained (W/O or O/W).

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM90™ by the company Goldschmidt. A crosslinked elastomeric solid organopolysiloxane comprising at least one oxyalkylene group, such as those obtained according to the procedure of Examples 3, 4 and 8 of U.S. Pat. No. 5,412,004 and of the examples of U.S. Pat. No. 5,811,487, especially the product of Example 3 (synthesis example) of U.S. Pat. No. 5,412,004, such as the product sold under the reference KSG 21 by the company Shin-Etsu, may also be used as surfactants for W/O emulsions.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

The fatty acid esters of a sugar that can be used as nonionic amphiphilic lipids can be chosen in particular from the group comprising esters or mixtures of esters of a $C_8$-$C_{22}$ fatty acid and of sucrose, of maltose, of glucose or of fructose, and esters or mixtures of esters of a $C_{14}$-$C_{22}$ fatty acid and of methylglucose.

The $C_8$-$C_{22}$ or $C_{14}$-$C_{22}$ fatty acids forming the fatty unit of the esters that can be used in the emulsion comprise a saturated or unsaturated linear alkyl chain having, respectively, from 8 to 22 or from 14 to 22 carbon atoms. The fatty unit of the esters can be chosen in particular from stearates, behenates, arachidonates, palmitates, myristates, laurates, caprates and mixtures thereof.

By way of example of esters or of mixtures of esters of a fatty acid and of sucrose, of maltose, of glucose or of fructose, mention may be made of sucrose monostearte, sucrose distearate, sucrose tristearate and mixtures thereof, such as the products sold by the company Croda under the name Crodesta F50, F70, F110 and F160 having, respectively, an HLB (Hydrophilic Lipophilic Balance) of 5, 7, 11 and 16; and, by way of example of esters or of mixtures of esters of a fatty acid and of methylglucose, mention may be made of the disearate of methylglucose and of polyglycerol-3, sold by the company Goldschmidt under the name Tego-care 450. Mention may also be made of glucose monoesters or maltose monoesters, such as methyl 0-hexadecanoyl-6-D-glucoside and O-hexadecanoyl-6-D-maltoside.

The fatty alcohol ethers of a sugar that can be used as nonionic amphiphilic lipids can be chosen in particular form the group comprising ethers or mixtures of ethers of a $C_8$-$C_{22}$ fatty alcohol and of glucose, of maltose, of sucrose or of fructose, and ethers or mixtures of ethers of a $C_{14}$-$C_{22}$ fatty alcohol and of methylglucose. They are in particular alkylpolyglucosides.

The $C_8$-$C_{22}$ or $C_{14}$-$C_{22}$ fatty alcohols forming the fatty unit of the ethers that can be used in the emulsion of the instant disclosure comprise a saturated or unsaturated linear alkyl chain having, respectively, from 8 to 22 or from 14 to 22 carbon atoms. The fatty unit of the ethers can be chosen in particular from decyl, cetyl, behenyl, arachidyl, stearyl, palmityl, myristyl, lauryl, capryl and hexadecanoyl units, and mixtures thereof such as cetearyl.

By way of example of fatty alcohol ethers of a sugar, mention may be made of alkylpolyglucosides, such as decylglucoside and laurylglucoside sold, for example, by the company Henkel under the respective names Plantaren 2000 and Plantaren 1200, cetostearylglucoside, optionally as a mixture with cetostearyl alcohol, sold, for example, under the name Montanov 68 by the company Seppic, under the name Tego-care CG90 by the company Goldschmidt and under the name Emulgade KE3302 by the company Henkel, and also arachidylglucoside, for example in the form of the mixture of arachidyl and behenyl alcohols and of arachidylglucoside sold under the name Montanov 202 by the company Seppic.

Use is more particularly made, as nonionic amphiphilic lipid of this type, of sucrose monostearate, sucrose distearate, sucrose tristearate and mixtures thereof, the distearate of methylglucose and of polyglycerol-3, and alkylpolyglucosides.

The glycerol fatty esters that can be used as nonionic amphiphilic lipids can be chosen in particular from the group comprising the esters formed from at least one acid comprising a saturated linear alkyl chain having from 16 to 22 carbon atoms, and from 1 to 10 glycerol units. Use may be made of one or more of these glycerol fatty esters in the emulsion of the instant disclosure.

These esters may be chosen in particular from stearates, behenates, arachidates, palmitates and mixtures thereof. Stearates and palmitates are preferably used.

By way of example of a surfactant that can be used in the emulsion of the instant disclosure, mention may be made of decaglycerol monostearate, distearate, tristearate and pentastearate (10 glycerol units) (CTFA names: polyglyceryl-10 stearate, polyglyceryl-10 distearate, polyglyceryl-10 tristearate, polyglyceryl-10 pentastearate), such as the products sold under the respective names Nikkol Decaglyn 1-S, 2-S, 3-S and 5-S by the company Nikko, and diglyceryl monostearate (CTFA name: polyglyceryl-2 stearate) such as the product sold by the company Nikko under the name Nikkol DGMS.

The sorbitan fatty esters that can be used as nonionic amphiphilic lipids chosen in particular from the group comprising esters of a $C_{16}$-$C_{22}$ fatty acid and of sorbitan and oxyethylenated esters of a $C_{16}$-$C_{22}$ fatty acid and of sorbitan. They are formed from at least one fatty acid comprising at least one saturated linear alkyl chain, having, respectively, from 16 to 22 carbon atoms, and from sorbitol or from ethoxylated sorbitol. The oxyethylenated esters generally comprise from 1 to 100 ethylene oxide units, and preferably from 2 to 40 ethylene oxide (EO) units.

These esters can be chosen in particular from stearates, behenates, arachidates, palmitates and mixtures thereof. Stearates and palmitates are preferably used.

By way of example of sorbitan fatty ester and of an oxyethylenated sorbitan fatty ester, mention may be made of sorbitan monostearate (CTFA name: sorbitan stearate) sold by the company ICI under the name Span 60, sorbitan monopalmitate (CTFA name: sorbitan palmitate) sold by the company ICI under the name Span 40, or sorbitan 20 EO tristearate (CTFA name: polysorbate 65) sold by the company ICI under the name Tween 65.

The ethoxylated fatty ethers are typically ethers made up of 1 to 100 ethylene oxide units and of at least one fatty alcohol chain having from 16 to 22 carbon atoms. The fatty chain of the ethers can be chosen in particular from behenyl, arachidyl, stearyl and cetyl units, and mixtures thereof, such as cetearyl. By way of example of ethoxylated fatty ethers, mention may be made of ethers of behenyl alcohol comprising 5, 10, 20 and 30 ethylene oxide units (CTFA names: beheneth-5, beheneth-10, beheneth-20 and beheneth-30), such as the products sold under the names Nikkol BBS, BB10, BB20 and BB30 by the company Nikko, and the ether of stearyl alcohol comprising 2 ethylene oxide units (CTFA name: steareth-2), such as the product sold under the name Brij 72 by the company ICI.

The ethoxylated fatty esters that can be used as nonionic amphiphilic lipids are esters made up of 1 to 100 ethylene oxide units and of at least one fatty acid chain comprising from 16 to 22 carbon atoms. The fatty chain of the esters can be chosen in particular from stearate, behenate, arachidate and palmitate units, and mixtures thereof. By way of example of ethoxylated fatty esters, mention may be made of the ester of stearic acid comprising 40 ethylene oxide units, such as the product sold under the name Myrj 52 (CTFA name: PEG-40 stearate) by the company ICI, and the ester of behenic acid comprising 8 ethylene oxide units (CTFA name: PEG-8 behenate), such as the product sold under the name Compritol HD5 ATO by the company Gattefosse.

The block copolymers of ethylene oxide and of propylene oxide that can be used as nonionic amphiphilic can be chosen in particular from poloxamers and in particular from Poloxamer 231, such as the product sold by the company ICI under the name Pluronic L81 of formula (V) with x=z=6, y=39 (HLB 2); Poloxamer 282, such as the product sold by the company ICI under the name Pluronic L92 of formula (V) with x=z=10, y=47 (HLB 6); and Poloxamer 124, such as the product sold by the company ICI under the name Pluronic L44 of formula (V) with x=z=11, y=21 (HLB 16).

As nonionic amphiphilic lipids, mention may also be made of the mixtures of nonionic surfactants described in document EP-A-705593, incorporated herein for reference.

Suitable hydrophobically-modified emulsifiers include, for example, inulin lauryl carbamate, commercially available from Beneo Orafti under the tradename Inutec SP1.

The total amount of emulsifiers in the sunscreen compositions, if present, may vary but are typically about 0.1 to about 30 wt. %, based on the total weight of the sunscreen composition. In some instances, the total amount of emulsifiers is about 0.1 to about 20 wt. %, about 0.1 to about 15 wt. %, about 0.1 to about 10 wt. %, about 0.5 to about 30 wt. %, about 0.5 to about 20 wt. %, about 0.5 to about 15 wt. %, about 0.5 to about 10 wt. %, about 1 to about 30 wt. %, about 1 to about 20 wt. %, about 1 to about 15 wt. %, about 1 to about 10 wt. %, or about 5 to about 5 wt. %, based on the total weight of the sunscreen composition.

Silicone Oils

The sunscreen compositions may optionally include one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Other examples of silicone oils that may be mentioned include volatile linear or cyclic silicone oils, especially those with a viscosity 8 centistokes ($8\times10^6$ m$^2$/s) and especially containing from 2 to 7 silicon atoms, these silicones optionally comprising alkyl or alkoxy groups containing from 1 to 10 carbon atoms. As volatile silicone oils that may be used in the disclosure, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The total amount of silicone oils in the sunscreen compositions, if present, can vary but is typically about 0.1 to about 40 wt. %, based on the total weight of the sunscreen composition. In some cases, the total amount of silicone oils in the sunscreen composition may be about 0.1 to about 30 wt. %, about 0.1 to about 20 wt. %, about 0.1 to about 10 wt. %, about 1 to about 40 wt. %, about 1 to about 30 wt. %, about 1 to about 20 wt. %, about 1 to about 10 wt. %, about 5 to about 40 wt. %, about 5 to about 30 wt. %, about 5 to about 20 wt. %, or about 5 to about 15 wt. %, based on the total weight of the sunscreen composition.

Forms

The form of the sunscreen compositions is not limited. For example, the sunscreen compositions may be in the form of a cream, a gel, a paste, a lotion, a rinse, a foam, an emulsion, a spray, etc. The sunscreen compositions may be prepared according to techniques that are well known to those skilled in the art, in particular those intended for the preparation of emulsions of oil-in-water or water-in-oil type. They may be in particular in the form of a simple or complex emulsion (O/W, W/O, O/W/O or W/O/W emulsion) such as a cream or a milk, in the form of a gel or a cream-gel, or in the form of a lotion.

EMBODIMENTS

The mineral sunscreen compositions do not require organic UV filtering agents. Therefore, in some embodiments, the mineral sunscreen compositions may be free or essentially free of UV filtering agents. In some embodiments, the mineral sunscreen compositions may be free or essentially free of butyl methoxydibenzoylmethane (avobenzone) and/or free or essentially free of ethylhexyl methoxycinnamate (octinoxate).

The combination of stilbenoids, ethylhexyl methoxycrylene, and diethylhexyl syringylidenemalonate in mineral sunscreen compositions boost the SPF of the mineral sunscreen composition. In some embodiments, mineral sunscreen compositions comprising stilbenoids, ethylhexyl methoxycrylene, and diethylhexyl syringylidenemalonate exhibit an in vitro SPF that is higher than the in vitro SPF of an otherwise identical mineral sunscreen composition without any one (or all) of stilbenoids, ethylhexyl methoxycrylene, and diethylhexyl syringylidenemalonate.

In Vitro SPF

SPF (sun protection factor) is a measure of how effective a sunscreen composition will be able to provide protection from ultraviolet B (UV-B) radiation. The chief cause of reddening and sunburn, UV-B rays tend to damage the epidermis, skin's outer layers. The in vitro SPF a can be determined using methods known in the art. Nonetheless, a preferable method for determining in vitro SPF is the method described in Fageon, L. et al. *Int. J. Cosmetic Sci.*, 2009, 405-17, which is incorporated herein by reference in its entirety.

Methods

The instant disclosure relates to methods for protecting a keratinous substrate, especially the skin and/or hair, from UV radiation, to methods of absorbing UV light, and to methods for preventing sunburn. Such methods comprise application of a sunscreen composition to a keratinous substrate, such as the skin and/or hair, and subjecting the keratinous substrate to ultraviolet radiation. Additionally, methods for boosting the SPF of mineral UV filtering agents and methods for reducing whiteness of mineral sunscreen compositions are encompassed. Such methods include combining an effective amount of stilbenoids, ethylhexylmethoxycrylene, and diethylhexyl syringylidenemalonate with one or more mineral UV filtering agents and formulating a sunscreen composition of the instant disclosure.

EMBODIMENTS

In some embodiments, the sunscreen compositions of the instant disclosure may include:
   (a) about 1 to about 25 wt. %, preferably about 1 to about 20 wt. %, more preferably about 5 to about 15 wt. % of one or more mineral UV filtering agents, for example, one or more mineral UV filtering agents selected from titanium dioxide, zinc oxide, iron oxides, cerium oxides, zirconium oxides, and a mixture thereof;
   (b) about 0.1 to about 8 wt. %, preferably about 0.1 to about 6 wt. %, more preferably about 0.1 to about 4 wt. % of one or more stilbenoids, for example, piceid, resveratrol, piceatannol, pterostilbene, or a mixture thereof; preferably piceid;
   (c) about 0.1 to about 8 wt. %, preferably about 0.1 to about 6 wt. %, more preferably about 0.1 to about 4 wt. % ethylhexylmethoxycrylene;
   (d) about 0.1 to about 7 wt. %, preferably about 0.1 to about 6 wt. %, more preferably about 0.1 to about 4 wt. % of diethylhexyl syringylidenemalonate; and
   (e) about 50 to about 95 wt. %, preferably about 60 to about 90 wt. %, more preferably about 70 to about 90 wt. % of a cosmetically acceptable carrier;
wherein all weight percentages are based on the total weight of the sunscreen composition.

The total amount of stilbenoids, ethylhexylmethoxycrylene, and diethylhexyl syringylidenemalonate in the sunscreen compositions can vary but is typically about 0.5 to about 10 wt. %, preferably about 0.5 to about 8 wt. %, more preferably about 1 to about 6 wt. %, based on the total weight of the sunscreen composition.

The weight ratio of piceid, ethylhexylmethoxycrylene, and diethylhexyl syringylidenemalonate relative to the total weight of the combination of piceid, ethylhexylmethoxycrylene, and diethylhexyl syringylidenemalonate may be as follows:
   about 0.1 to about 0.5, preferably about 0.1 to about 0.4, more preferably about 0.2 to about 0.4 of the one or more stilbenoids;
   about 0.25 to about 0.75, preferably about 0.3 to about 0.7, more preferably about 0.3 to about 0.6 of ethylhexylmethoxycrylene; and
   about 0.1 to 0.5, preferably about 0.1 to about 0.45, more preferably about 0.15 to about 0.4 of diethylhexyl syringylidenemalonate.

Furthermore, ethylhexylmethoxycrylene, and diethylhexyl syringylidenemalonate are typically in amounts sufficient to boost the in vitro SPF of the sunscreen composition by at least 5%, preferably at least 8%, more preferably at least 10%, in comparison to an otherwise identical sunscreen composition in which the total amount of the stilbenoid(s), ethylhexylmethoxycrylene, and diethylhexyl syringylidenemalonate is replaced with only ethylhexylmethoxycrylene.

The stilbenoid(s), ethylhexylmethoxycrylene, and diethylhexyl syringylidenemalonate are typically in amounts sufficient to boost the in vitro SPF of the sunscreen composition by at least 5%, preferably at least 10%, more preferably at least 20%, in comparison to an otherwise identical sunscreen composition in which the total amount of the stilbenoid(s), ethylhexylmethoxycrylene, and diethylhexyl syringylidenemalonate is replaced with only diethylhexyl syringylidenemalonate.

The sunscreen composition may be free or essentially free of organic UV filtering agents. In some instances, the sunscreen composition is free or essentially free of at least butyl methoxydibenzoylmethane (avobenzone) and ethylhexyl methoxycinnamate (octinoxate).

In additional embodiments, the sunscreen compositions include:
   (a) about 1 to about 25 wt. %, preferably about 1 to about 20 wt. %, more preferably about 5 to about 15 wt. % of one or more mineral UV filtering agents, for example, one or more mineral UV filtering agents selected from titanium dioxide, zinc oxide, iron oxides, cerium oxides, zirconium oxides, and a mixture thereof;
   (b) at least 0.2 wt. %, preferably at least 0.2 wt. % to about 6 wt. %, more preferably at least 0.2 wt % to about 3 wt. % of one or more stilbenoids, for example, piceid, resveratrol, piceatannol, pterostilbene, or a mixture thereof; preferably piceid;
   (c) at least 0.5 wt. %, preferably at least 0.5 to about 8 wt. %, more preferably at least 0.5 to about 5 wt. % of ethylhexylmethoxycrylene;
   (d) at least 0.2 wt. %, preferably at least about 0.2 to about 6 wt. %, more preferably about 0.2 to about 2 wt. % of diethylhexyl syringylidenemalonate;
   wherein the total amount of the stilbenoid(s), ethylhexylmethoxycrylene, and diethylhexyl syringylidenemalonate does not exceed 10 wt. %, preferably 6 wt. %, more preferably 4 wt. %; and
   (e) about 50 to about 95 wt. %, preferably about 60 to about 90 wt. %, more preferably about 70 to about 90 wt. % of a cosmetically acceptable carrier; wherein the cosmetically acceptable carrier preferably includes water;
wherein all weight percentages are based on the total weight of the sunscreen composition.

The weight ratio of the piceid, ethylhexylmethoxycrylene, and diethylhexyl syringylidenemalonate relative to the total weight of the combination of piceid, ethylhexylmethoxycrylene, and diethylhexyl syringylidenemalonate may be as follows:
   about 0.1 to about 0.5, preferably about 0.1 to about 0.4, more preferably about 0.2 to about 0.4 of the one or more stilbenoids;
   about 0.25 to about 0.75, preferably about 0.3 to about 0.7, more preferably about 0.3 to about 0.6 of ethylhexylmethoxycrylene; and
   about 0.1 to 0.5, preferably about 0.1 to about 0.45, more preferably about 0.15 to about 0.4 of diethylhexyl syringylidenemalonate.

Furthermore, ethylhexylmethoxycrylene, and diethylhexyl syringylidenemalonate are typically in amounts sufficient to boost the in vitro SPF of the sunscreen composition by at least 5%, preferably at least 8%, more preferably at least 10%, in comparison to an otherwise identical sunscreen composition in which the total amount of the stilbenoid(s), ethylhexylmethoxycrylene, and diethylhexyl syringylidenemalonate is replaced with only ethylhexylmethoxycrylene.

The stilbenoid(s), ethylhexylmethoxycrylene, and diethylhexyl syringylidenemalonate are typically in amounts sufficient to boost the in vitro SPF of the sunscreen composition by at least 5%, preferably at least 10%, more preferably at least 20%, in comparison to an otherwise identical sunscreen composition in which the total amount of the stilbenoid(s), ethylhexylmethoxycrylene, and diethylhexyl syringylidenemalonate is replaced with only diethylhexyl syringylidenemalonate.

The sunscreen composition may be free or essentially free of organic UV filtering agents. In some instances, the sunscreen composition is free or essentially free of at least butyl methoxydibenzoylmethane (avobenzone) and ethylhexyl methoxycinnamate (octinoxate).

The instant disclosure will be better understood from the examples that follow, all of which are intended for illustrative purposes only and are not meant to limit the scope of the instant disclosure in any way.

Example 1

The influence of stilbenoids (piceid), ethylhexyl methoxycrylene, and diethylhexyl syringylidenemalonate on in vitro SPF of mineral sunscreen compositions was investigated. These three components were used in various ratios with respect to one another. The three components were added into the base sunscreen composition in a total amount of 3 wt. %, based on the total weight of the final sunscreen composition, regardless of the ratio of the three components used. Details for the sunscreen compositions are provided in the table below.

| Phase | Raw material | 100 g |
|---|---|---|
| A | WATER | Q.S. |
|  | Piceid (Polydatin) | Varies |
|  | SODIUM CHLORIDE | 0.50 |
|  | DISODIUM EDTA | 0.10 |
|  | HYDROTROPES | ≤3 |
| B | EMOLLIENTS | 30-40 |
|  | STRUCTURING AGENTS | 2.0-5.0 |
|  | PRESERVATIVE | 1.0-5.0 |
|  | EMULSIFIER | 4.5-6.5 |
| B1 | TITANIUM DIOXIDE | 10.2 |
| C | TOCOPHEROL | 0.1-1.0 |
| D | ETHYLHEXYL METHOXYCRYLENE | Varies |
| E | CITRIC ACID | 0.50 |
| F | DIETHYLHEXYL SYRINGYLIDENEMALONATE | Varies |

The sunscreen compositions may be prepared by adding the ingredients of phase B into a main beaker and heating to about 70° C., while mixing. Phase B1 is added to phase B and the mixture becomes more clear. The mixture is homogenized for 20 minutes. In a separate beaker, the ingredients of phase A are combined and heated to about 70° C., while mixing. Phase A is added into phase B and the combination is homogenized for 20 minutes while maintaining the temperature at about 70° C. The combination is then allowed to begin to cool to room temperature. While cooling, when the mixture reaches about 60° C., phase C is added and the mixture is homogenized for about 2 minutes. When the mixture reaches about 50° C., phase D is added and the mixture is homogenized for about 3 minutes. When the mixture reaches about 45° C., phase E is added and the mixture mixed for about 5 minutes. When the mixture reaches about 40° C., phase F is added and the mixture is homogenized for about 5 minutes.

In vitro SPF was measured for the resulting sunscreen formulations using a method adapted from Fageon, L. et al. *Int. J. Cosmetic Sci.*, 2009, 405-17. Samples weighing 30 mg were transferred by an adjustable pipette and uniformly applied to sand-blasted PMMA (polymethyl methacrylate) plates (roughness 6 μm) measuring 5 cm by 5 cm by about 6 mm thick. The sample was uniformly applied to the plate with a finger inside a fingercot using a series of circular motions followed by side-to-side motions in a regular and controlled fashion such that the amount of product remaining on the plate following application described in this manner weighed approximately 15-20 mg. The plate was dried at room temperature for 15 to 20 minutes and the in vitro SPF was measured using a Labsphere Ultraviolet Transmittance Analyzer (Model UV-2000 available from the Solar Light Company, Philadelphia, Pa.). The SPF of each plate was recorded as an average of 5 measurements across different areas of the plate. The SPF for each formulation was recorded as an average of at least two plates.

The results of various mixtures of piceid, ethylhexyl methoxycrylene, and diethylhexyl syringylidenemalonate were investigated using a design of experiments approach, wherein 16 sunscreen formulas were prepared containing mineral UV filtering agents (prepared as described above) each contained a total of 3 wt. % percent by weight of a mixture of piceid, ethylhexyl methoxycrylene, and diethylhexyl syringylidenemalonate. The details of the 3 wt. % mixtures are detailed in the table below. The amount of piceid, ethylhexyl methoxycrylene, and diethylhexyl syringylidenemalonate are represented in the table below as the weight ratio of the amount of each individual ingredient compared to the total amount of the mixture of piceid, ethylhexyl methoxycrylene, and diethylhexyl syringylidenemalonate. For example, mixture #1 included 45 wt. % of piceid, 10 wt. % of ethylhexyl methoxycrylene, and 45 wt. % of diethylhexyl syringylidenemalonate, based on the total weight of the piceid, ethylhexyl methoxycrylene, and diethylhexyl syringlidenemalonate. Mixture #1 was used in the base sunscreen composition described above in an amount of 3 wt. %, based on the total weight of the sunscreen composition.

| # | Piceid (Polydatin) | Ethylhexyl Methoxycrylene | Diethylhexyl Syringylidenemalonate | SPF Measured[1] |
|---|---|---|---|---|
| 1 | 0.45 | 0.1 | 0.45 | 26.63 |
| 2 | 0.05 | 0.66 | 0.29 | 50.94 |
| 3 | 0.45 | 0.5 | 0.05 | 39.53 |
| 4 | 0.29 | 0.66 | 0.05 | 36.53 |
| 5 | 0.05 | 0.5 | 0.45 | 43.09 |
| 6 | 0.05 | 0.58 | 0.37 | 36.36 |
| 7 | 0.45 | 0.3 | 0.25 | 31.6 |
| 8 | 0.17 | 0.66 | 0.17 | 37.31 |
| 9 | 0.37 | 0.58 | 0.05 | 52.74 |
| 10 | 0.25 | 0.3 | 0.45 | 40.09 |
| 11 | 0.26 | 0.48 | 0.26 | 72.17 |
| 12 | 0.33 | 0.33 | 0.33 | 66.32 |
| 13 | 0.18 | 0.52 | 0.3 | 72.84 |
| 14 | 0.3 | 0.53 | 0.17 | 64.05 |

[1]In vitro SPF measured on PMMA plates according to the procedure above. The measured in vitro SPF was used to build the multiple linear regression model.

Figure 1:
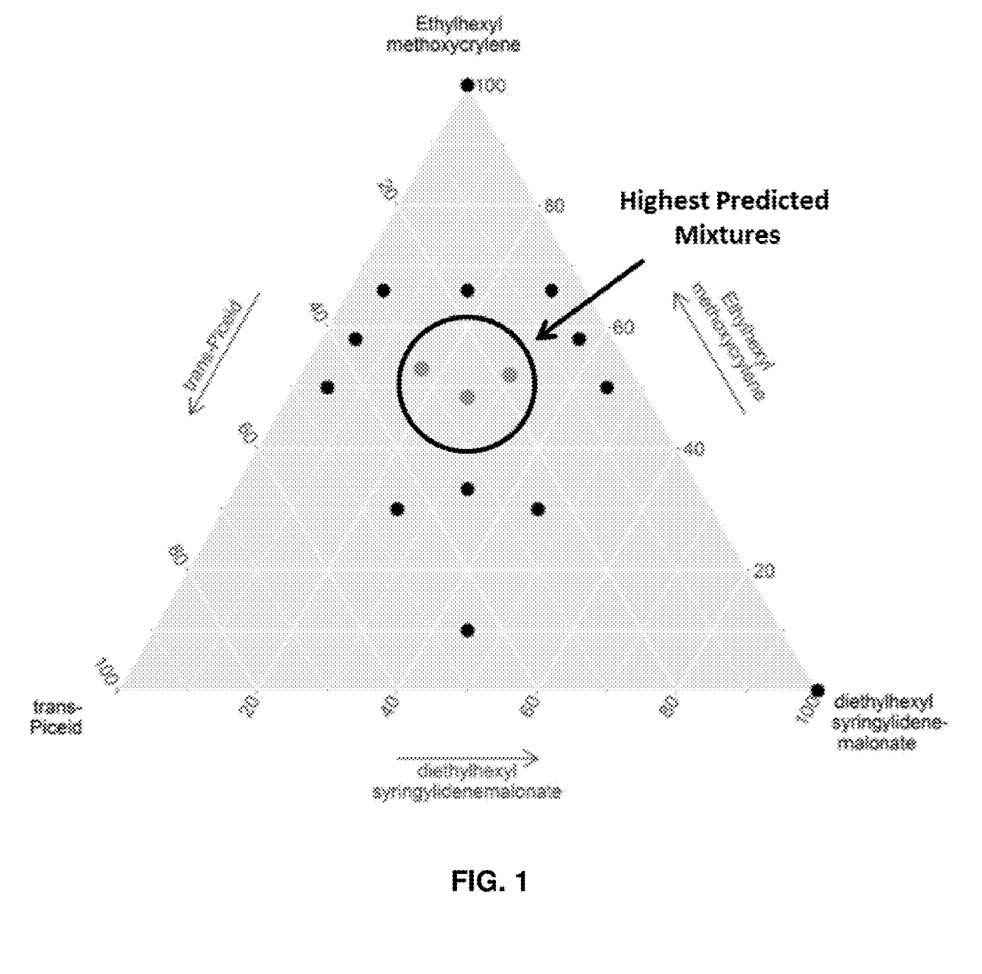
FIG. 1 is a contour plot of the predicted SPF values for mineral sunscreen comprising mixtures of piceid (X2), ethylhexylmethoxycrylene (X1), and diethylhexyl syringylidenemalonate (X3)
Figure 2:
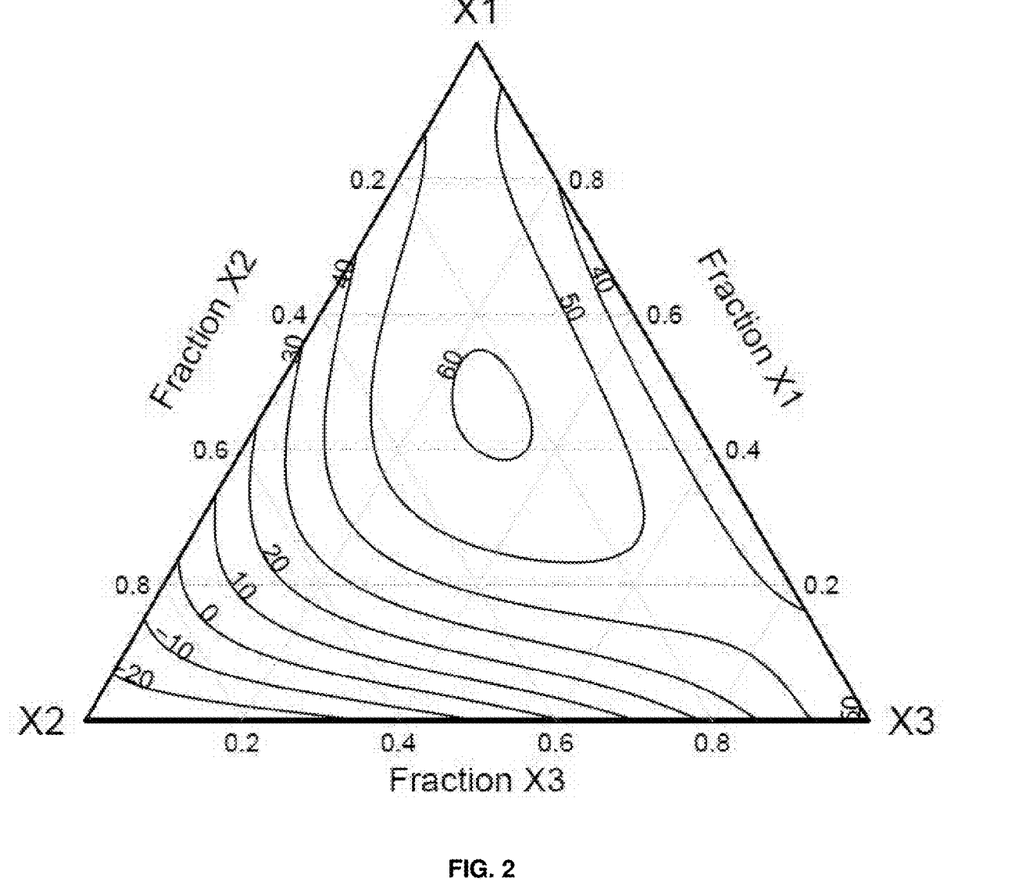
FIG. 2 is a diagram showing the mixtures outlined in the Examples which were used to build a linear regression model to explain the impact of piceid, ethyhexylmethoxycrylene, and diethylhexyl syringylidenemalonate on the mineral sunscreen composition, highlighting the particular mixtures that demonstrate the highest SPF in vitro and highest predicted SPF compared to the other mixtures prepared.

The measured SPF values of the 16 formulations in the table above were used to predict the SPF of all possible mixtures of piceid, ethylhexyl methoxycrylene, and diethylhexyl syringylidenemalonate by fitting the dataset to a multiple linear regression model (multiple R-squared value >0.99). The multiple linear regression model was used to predict the in vitro SPF of about 24,000 simulated combinations of piceid, ethylhexyl methoxycrylene, and diethylhexyl syringylidenemalonate, used alone or as a mixture, when added to the sunscreen at 3 wt. %. The about 24,000 simulated combinations included mixtures containing one, two, or all of piceid, ethylhexyl methoxycrylene, and diethylhexyl syringylidenemalonate. Surprisingly, compositions 11, 12, 13, and 14 were predicted to have the highest in vitro SPF out of all combinations. The in vitro SPF of inventive compositions 11, 12, 13, and 14, were compared with compositions C-1 and C-2. For reference, Composition C-1 included ethylhexyl methoxycrylene but not stilbenoids (piceid) and diethylhexyl syringylidenemalonate. Composition C-2 included diethylhexyl syringylidenemalonate but not stilbenoids (piceid) and ethylhexyl methoxycrylene. The results of the example inventive compositions 11, 12, 13, and 14, along with the comparative compositions C-1 and C-2, are shown in the table below, and exemplify the use of the inventive combination to yield a measured in vitro SPF value above that which is attainable using either ethylhexyl methoxycrylene or diethylhexyl syringylidenemalonate alone. Additionally, FIG. 1. Illustrates a contour plot of the linear regression model which demonstrates the inventive combinations yield predicted SPF values above that which is attainable using either ethylhexylmethoxycrylene along, diethylhexyl syringylidenemalonate alone, or mixtures thereof.

comparison to an otherwise identical sunscreen composition in which the total amount of the piceid, the ethylhexylmethoxycrylene, and the diethylhexyl syringylidenemalonate is replaced with only ethylhexylmethoxycrylene.

5. The sunscreen composition of claim 1, wherein the piceid, the ethylhexylmethoxycrylene, and the diethylhexyl syringylidenemalonate are in amounts sufficient to boost the in vitro SPF of the sunscreen composition by at least 5% in comparison to an otherwise identical sunscreen composition in which the total amount of the piceid, the ethylhexylmethoxycrylene, and the diethylhexyl syringylidenemalonate is replaced with only diethylhexyl syringylidenemalonate.

6. The sunscreen composition of claim 1, wherein the sunscreen composition is free of butyl methoxydibenzoylmethane (avobenzone) and ethylhexyl methoxycinnamate (octinoxate).

7. The sunscreen composition of claim 1, wherein the sunscreen composition is free of organic UV filtering agents.

8. The sunscreen composition of claim 1, wherein the total amount of the one or more inorganic UV filtering agents is from about 1 to about 25 wt. %, based on the total weight of the sunscreen composition.

|     | IUPAC | 11 | 12 | 13 | 14 | C-1 | C-2 |
| --- | --- | --- | --- | --- | --- | --- | --- |
| (a) | Piceid (Polydatin) | 0.258 | 0.33 | 0.18 | 0.3 | 0 | 0 |
| (b) | Ethylhexyl Methoxycrylene | 0.484 | 0.33 | 0.52 | 0.53 | 1 | 0 |
| (c) | Diethylhexyl Syringylidenemalonate | 0.258 | 0.33 | 0.3 | 0.17 | 0 | 1 |
|     | Total Amount of (a), (b), and (c)[2] | 3 wt % | 3 wt % | 3 wt % | 3 wt % | 3 wt % | 3 wt % |
|     | Measured In vitro SPF [1] | 72.17 | 66.32 | 72.84 | 64.05 | 57.95 | 52.29 |

[1] In vitro SPF measured on PMMA plates.
[2] The total amount of (a), (b), and (c) in all sunscreen formulations was 3 wt. %, based on the total weight of the sunscreen composition. The numbers representing the amount of (a), (b), and (c) in the table above reflect the weight ratio of each designated ingredient, based on the total amount of (a), (b), and (c).

The invention claimed is:

1. A sunscreen composition comprising:
   (a) one or more mineral UV filtering agents;
   (b) piceid;
   (c) ethylhexylmethoxycrylene;
   (d) diethylhexyl syringylidenemalonate; and
      wherein weight ratios for the piceid, the ethylhexylmethoxycrylene, and the diethylhexyl syringylidenemalonate relative to the total weight of the combination of the piceid, the ethylhexylmethoxycrylene, and the diethylhexyl syringylidenemalonate is as follows:
      0.1 to 0.4 for the piceid,
      0.3 to 0.53 for the ethylhexylmethoxycrylene; and
      0.1 to 0.4 for the diethylhexyl syringylidenemalonate
   (e) a cosmetically acceptable carrier.

2. The sunscreen composition of claim 1, wherein the one or more mineral UV filtering agents are selected from titanium dioxide, zinc oxide, iron oxides, cerium oxides, zirconium oxides, and a mixture thereof.

3. The sunscreen composition of claim 1, wherein the total amount of the piceid, the diethylhexyl syringylidenemalonate, and the ethylhexylmethoxycrylene in the sunscreen composition is about 0.5 wt. % to about 6 wt. %, based on the total weight of the sunscreen composition.

4. The sunscreen composition of claim 1, wherein the piceid, the ethylhexylmethoxycrylene, and the diethylhexyl syringylidenemalonate are in amounts sufficient to boost the in vitro SPF of the sunscreen composition by at least 5% in 9. A sunscreen composition of claim 1 comprising:
   (a) one or more mineral UV filtering agents:
   (b) at least 0.2 wt. % of piceid:
   (c) at least 0.5 wt. % of ethylhexylmethoxycrylene: and
   (d) at least 0.2 wt. % of diethylhexyl syringylidenemalonate,
      wherein the weight percentages are based on the total weight of the sunscreen composition: and wherein the total amount of the piceid, the ethylhexylmethoxycrylene, and the diethylhexyl syringylidenemalonate does not exceed 6 wt. %, based on the total weight of the sunscreen composition.

10. A sunscreen composition of claim 1 comprising:
    (a) one or more mineral UV filtering agents;
    (b) about 0.2 to about 3 wt % of piceid;
    (c) about 0.5 to about 5 wt. % of ethylhexylmethoxycrylene; and
    (d) about 0.2 to about 2 wt. % of diethylhexyl syringylidenemalonate,
       wherein the weight percentages are based on the total weight of the sunscreen composition.

11. The sunscreen composition of claim 1, wherein the piceid, the ethylhexylmethoxycrylene and the diethylhexyl syringylidenemalonate are in amounts sufficient to:
    boost the in vitro SPF of the sunscreen composition by at least 5% in comparison to an otherwise identical sunscreen composition in which the total amount of the piceid, the ethylhexylmethoxycrylene, and the diethylhexyl syringylidenemalonate is replaced with only ethylhexylmethoxycrylene; and boost the in vitro SPF of the sunscreen composition by at least 5% in comparison to an otherwise identical sunscreen composition in which the total amount of the piceid, the ethylhexylmethoxycrylene, and the diethylhexyl syringylidenemalonate is replaced with only diethylhexyl syringylidenemalonate.

12. The sunscreen composition of claim 1, further comprising:
(f) one or more silicone oils.

13. The sunscreen composition of claim 1 in the form of a lotion, cream, gel, or spray.

14. The sunscreen composition of claim 1, wherein the cosmetically acceptable carrier comprises water.

15. The sunscreen composition of claim 1 in the form of an emulsion.

16. A sunscreen composition comprising:
(a) about 1 to about 25 wt. %, based on the total weight of the sunscreen composition, of one or more mineral UV filtering agents selected from titanium dioxide, iron oxide, and a mixture thereof;
(b) piceid;
(c) ethylhexylmethoxycrylene; and
(d) diethylhexyl syringylidenemalonate;
wherein the total amount of the combination of the piceid, the ethylhexylmethoxycrylene, and the diethylhexyl syringylidenemalonate is from about 1 wt % to about 6 wt %, based on the total weight of the sunscreen composition; and
weight ratios for the piceid, the ethylhexylmethoxycrylene, and the diethylhexyl syringylidenemalonate relative to the total weight of the combination of piceid, the ethylhexylmethoxycrylene, and the diethylhexyl syringylidenemalonate is as follows:
0.1 to about 0.4 for the piceid;
0.3 to 0.53 for the ethylhexylmethoxycrylene; and
about 0.1 to 0.4 for the diethylhexyl syringylidenemalonate.

17. A method for protecting skin from UV radiation comprising applying an effective amount of the sunscreen composition of claim 1 to the skin.

* * * * *